United States Patent [19]
Sheridan

[11] Patent Number: 5,687,740
[45] Date of Patent: Nov. 18, 1997

[54] NEEDLE HOLDER ASSEMBLY INCLUDING SLEEVE OF THERMOPLASTIC ELASTOMER

[75] Inventor: Martin F. Sheridan, Wayne, N.J.

[73] Assignee: Becton, Dickinson and Company, Franklin Lakes, N.J.

[21] Appl. No.: 496,711

[22] Filed: Jun. 29, 1995

[51] Int. Cl.[6] .................................................. A61B 5/00
[52] U.S. Cl. .................................................. 128/760; 604/195
[58] Field of Search .................................. 604/110, 194–198, 604/208–210, 263; 128/760

[56] References Cited

U.S. PATENT DOCUMENTS 4,879,098  11/1989  Oberhardt et al. .
5,033,476   7/1991  Kasai ....................................... 128/764
5,328,473   7/1994  Fayngold et al. ........................ 604/110
5,423,758   6/1995  Shaw ....................................... 604/110

*Primary Examiner*—Robert A. Hafer
*Assistant Examiner*—Pamela L. Wingood
*Attorney, Agent, or Firm*—Richard E. Brown

[57] ABSTRACT

A needle holder assembly for taking a blood sample with an evacuated tube includes a needle affixed to a hub and a tubular needle holder removably affixed to the hub. A thermoplastic elastomeric sleeve fits snugly over one end of the needle and is punctured by the needle during sampling and is resealed upon withdrawal of the evacuated tube. The invention includes a method to mold the sleeve.

3 Claims, 3 Drawing Sheets

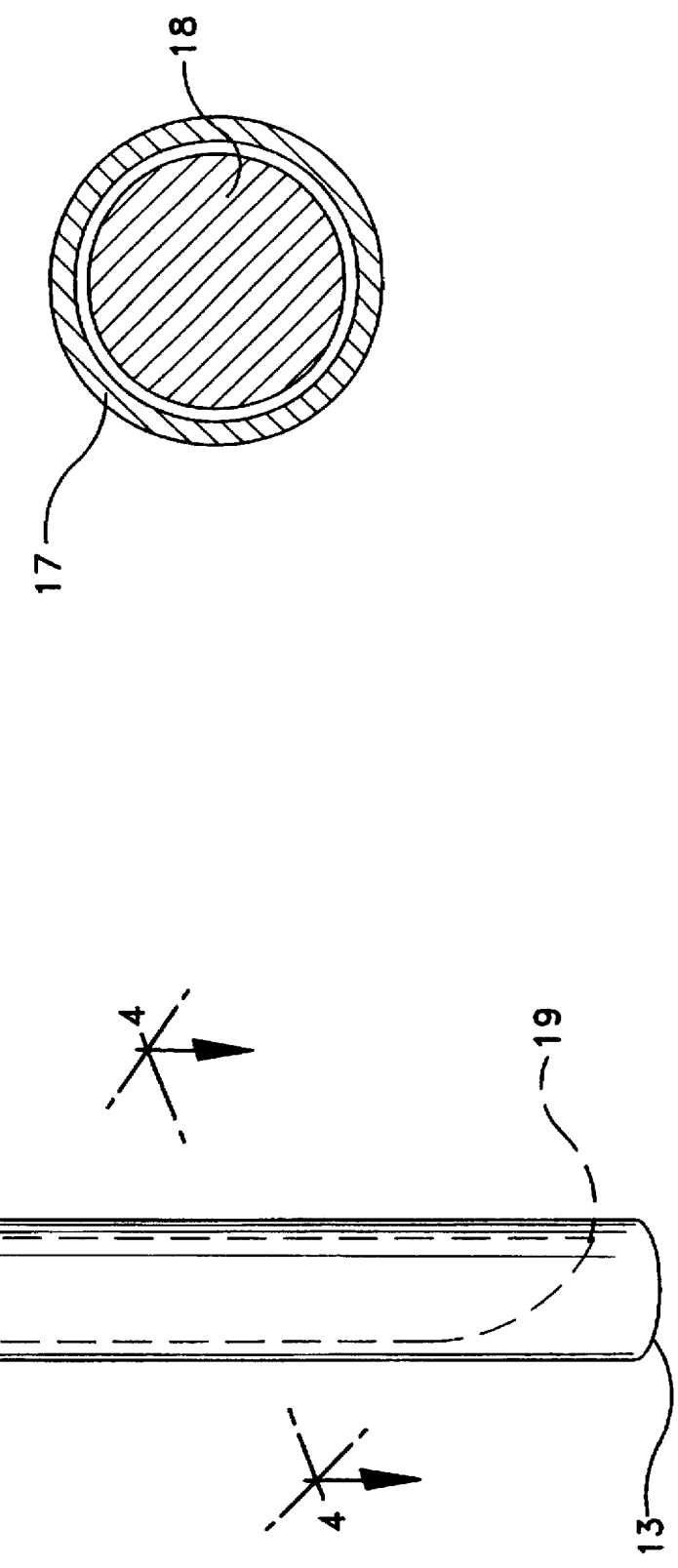

5,687,740

NEEDLE HOLDER ASSEMBLY INCLUDING SLEEVE OF THERMOPLASTIC ELASTOMER

BACKGROUND OF THE INVENTION

1. Field of the Invention

This invention relates to blood sample collection, and more particularly relates to an improved sleeve for a blood draw needle used with evacuated tubes and method therefor.

2. Background

Blood samples are conventionally taken with evacuated tubes, such as those sold under the trade name VACU-TAINER# by Becton, Dickinson and Company. Evacuated tubes have a closed end and an open end with a closure therein and are used in conjunction with a needle holder assembly. Needle holder assemblies include a hollow, cylindrical inner tubular body (the needle holder) and a single-ended or double-ended needle. A proximal end of the needle extends into the needle holder and is covered with a flexible sleeve. A distal end of the needle extends outwardly from the needle holder for insertion into a patient's vein.

During sample collection, the evacuated tube is inserted into the needle holder and advanced forward so that the proximal end of the needle pierces both the sleeve and the closure. The vacuum in the tube draws the blood sample through the needle into the tube. When the sample has been collected, the tube is removed from the holder. For multiple sample collection, the process is repeated with subsequent tubes. When the last tube has been filled, the entire assembly is removed from the patient's arm and discarded. A representative needle holder assembly is disclosed in U.S. Pat. No. 5,328,473 to Fayngold et al.

Sleeves for the proximal end of the needle have conventionally been made of thermoset natural (polyisoprene) rubber. However, because the polyisoprene is thermoset, a cycle time of up to five minutes during molding is required for cross-linking and leads to low productivity during the manufacturing process, and the flash inherent in the molding process is nonrecyclable. The present invention is directed to overcoming these problems.

SUMMARY OF THE INVENTION

One aspect of the invention is a needle holder assembly for collection of body fluid samples using evacuated tubes. The assembly includes a needle, either single- or double-ended, securely immobilized in a hub and a tubular needle holder to which the hub is removably affixed. A proximal end of the needle is positioned within the holder and has a resilient and resealable sleeve of a thermoplastic elastomer (TPE) fitted snugly thereover. A distal end of the needle extends outwardly from the hub for puncture of a patient's skin or connection to a conventional Leur# lock.

A second aspect of the invention is a method to mold the TPE sleeve of the invention by injection, compression or transfer molding.

In use, a conventional evacuated sample collection tube is advanced into the holder until the tube closure abuts the sleeve over the proximal end of the needle. Further advancement of the tube causes the needle point to puncture first the sleeve and then the closure so that fluid communication from the patient to the interior of the evacuated tube is established and body fluid is drawn into the tube by the pressure differential between the tube and the patient. When sample collection is complete, the tube is withdrawn. The sleeve, because of the resiliency of the TPE, returns to its original position over the needle point and the puncture in the sleeve reseals. Additional samples may then be taken in subsequent evacuated tubes, the sleeve performing with each tube to reseal and prevent leakage of body fluid during tube changeover.

The TPE sleeve of the invention has excellent compression during puncture, resiliency for return to the original position, and resealability for prevention of any substantial blood leakage during multiple tube changeovers. The TPE sleeve may be manufactured in a cycle time at least fivefold less than that required to make conventional thermoset polyisoprene sleeves, and, because of the thermoplasticity, the molding flash is recyclable. The short cycle time and recyclability provide greatly improved productivity during manufacture with significant cost savings.

BRIEF DESCRIPTION OF THE DRAWINGS

FIG. 3 is a perspective view of the sleeve and cannula (in phantom) of FIG. 2; and FIG. 4 is a cross-sectional view of the sleeve of FIG. 3 taken along the line 4—4 thereof.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Figure 1A:
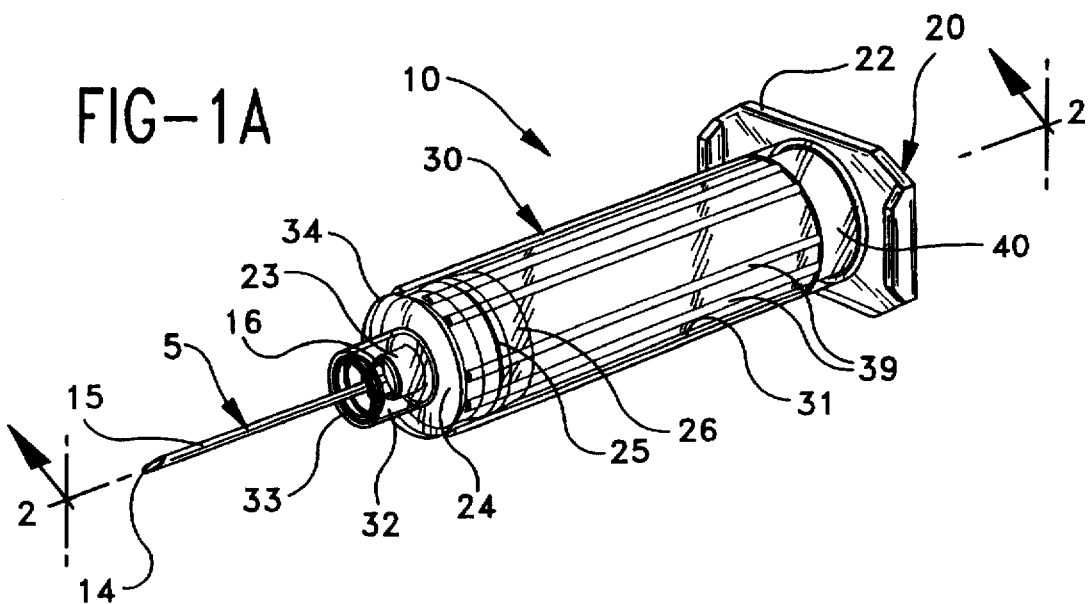
FIG. 1A is a perspective view of a preferred needle holder assembly of the present invention in a retracted position.
Figure 1B:
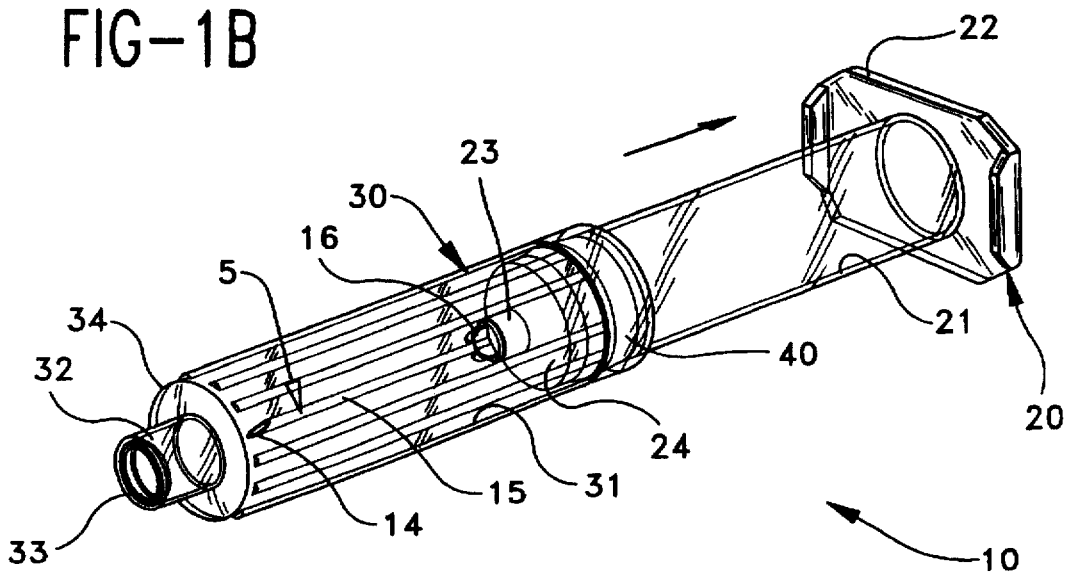
FIG. 1B is a perspective view of the needle holder assembly shown in FIG. 1A in an extended position.
Figure 2:
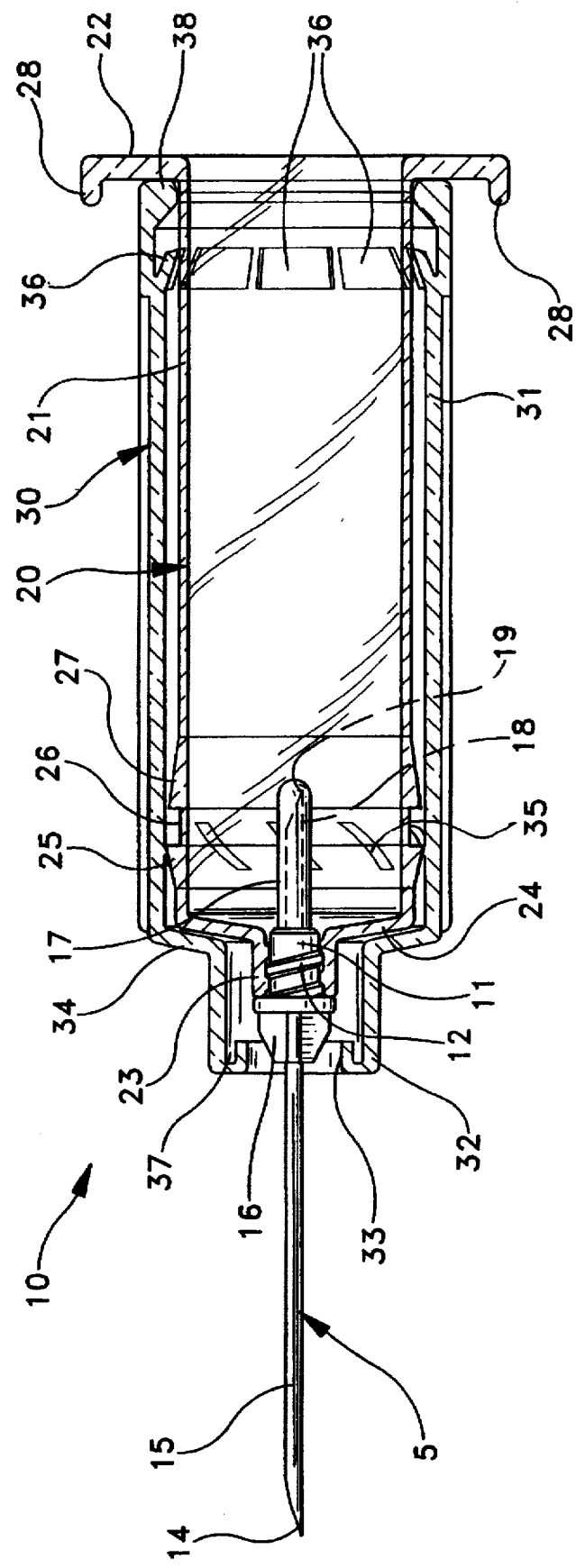
FIG. 2 is a cross-sectional view of the needle holder assembly shown in FIG. 1A taken along the line 2—2 thereof.

The sleeve of the invention may be used with any conventional needle holder assembly as known in the art for taking body fluid samples, particularly blood, using evacuated tubes. The assembly may include a needle securely affixed to a hub removably attached to a needle holder. FIGS. 1A, 1B and 2 illustrate a preferred assembly having a double-ended needle.

Needle holder assembly 10 generally includes a needle assembly 5, a needle holder 20 and an optional outer safety shield 30. Needle holder 20 is slidably received within a proximal open end 40 of outer shield 30. After blood sampling is complete, the assembly may be locked in the extended position of FIG. 1B so that the needle is completely enclosed for safe disposal.

Needle holder 20 includes a cylinder wall 21 having a flange 22 with a pair of tabs 28 at its proximal end and a shoulder 24 at its distal end tapering to a threaded neck 23. Neck 23 has threads that mate with a matching thread 12 on a base 11 of the needle assembly 5 to securely hold needle assembly 5 in holder 20. Needle holder 20 also includes a pair of ramps 25 and 27 with a groove 26 positioned there between which are shown in more detail in FIG. 2 described below.

Outer shield 30 includes a wall 31 extending axially from a distal end to a proximal end with a plurality of ribs 39 extending longitudinally on an outer surface of wall 31. A shoulder 34 at the distal end of outer wall 31 tapers to an annular cylindrical neck 32 having an annular toroid-shaped channel 33 at 15 and a proximal end 18. A distal needle point 14 extends beyond neck 32 and channel 33 when needle holder 20 is in the retracted position shown in FIG. 1A so that point 14 is ready to pierce a patient to draw a sample of body fluid. Assembly 5 may include an optional and conventional needle safety shield, not shown in the drawing, which may conveniently be removably affixed to a needle hub 16.

As shown in FIG. 2, base 11 on needle hub 16 of needle assembly 5 is screwed into neck 23 of needle holder 20. In particular, thread 12 on base 11 of needle hub 16 mates with the thread in neck 23 to firmly attach needle assembly 5 to needle holder 20. When needle assembly 5 has been attached to needle holder 20, distal needle portion 15 extends out of neck 23 so that distal needle point 14 can be used to pierce a patient's skin. Proximal portion 18 (shown in phantom) includes a needle point 19 and extends into needle holder 20. Proximal portion 18 is located in a flexible sleeve 17, which seals 18 to prevent body fluid from flowing into needle holder 20. However, when an evacuated tube (not shown in the drawings) is mounted in needle holder 20, a closure on the tube is pierced by point 19. Sleeve 17 is also pierced and pushed down proximal portion 18 to allow body fluid to flow through needle portions 15 and 18 into the tube in holder 20. When the tube has drawn the desired amount of body fluid it is removed, permitting resilient sleeve 17 to return to its original position and again seal proximal portion 18. Additional tubes can then be inserted sequentially into holder 20 to draw additional body fluid samples.

A shoulder 24 of needle holder 20 abuts the interior surface of shoulder 34 on shield 30 when assembly 10 is in the retracted position. Contact between shoulders 24 and 34 prevents holder 20 from advancing any further in the distal direction. To prevent holder 20 from sliding in the proximal direction, a plurality of lead threads 35 on shield 30 mate with ramp 25 on the outer surface of cylinder wall 21 on holder 20. The interaction between lead threads 35 and ramp 25 retain holder 20 in the retracted position and prevent in the distal direction. To prevent holder 20 from sliding in the proximal direction, a plurality of lead threads 35 on shield 30 mate with ramp 25 on the outer surface of cylinder wall 21 on holder 20. The interaction between lead threads 35 and ramp 25 retain holder 20 in the retracted position and prevent it from unintentionally sliding out of position. Maintaining holder 20 is the retracted position within shield 30 is particularly important when needle assembly 5 is being screwed into holder 20 and assembly 10 is being transported prior to use. The plurality of lead threads 35 and ramp 25 also combine to provide a release mechanism for assembly 10 that smoothly releases needle holder 20 from the retracted position when holder 20 is rotated in a counter-clockwise direction. Sleeve 17, illustrated in more detail in FIGS. 3 and 4, is shown to fit snugly around proximal portion 18. Closed end 13 of sleeve 17 surrounds point 19, and, as described, is punctured by point 19 when the closure of an evacuated tube is advance firmly against end 13 during sample collection.

Needle safety shields which serve only for safe disposal after use and for protection against inadvertent needle stick have few material requirements. For such shields no criticality is associated with material selection. In contrast, the needle sleeve of the invention designed to cover the needle point in a needle holder assembly and intended for blood sample collection using evacuated tubes must have excellent flexibility, resiliency, puncturability and sealability for reliable leak-free multiple sampling. Because of these stringent performance requirements, such sleeves have conventionally been made of thermoset polyisoprene. While needle sleeves of thermoset polyisoprene perform well in a needle holder, manufacturing drawbacks, in particular long cycle time, with this material cause substantial cost increases.

It has now been found that needle sleeves made from certain TPEs are suitable for use with evacuated tubes in a needle holder assembly. In addition, the sleeve can be manufactured by simple thermoplastic processing techniques of short cycle time with no loss of material because the molding flash is all recyclable.

In order to achieve the resiliency and resealability required of the sleeve of the invention, the TPE must have a durometer hardness on the A scale of about 30–60, a tensile strength at break of about 300–1,000 psi and an elongation at break of about 200–800% Styrene-butadiene copolymers meeting these limits, as for example, styrene-ethylene-butadiene-styrene copolymer (sold under the trade name KRATON® by Shell Chemical Company) are suitable. Vulcanized alloys of polyethylene or polypropylene with terpolymers of ethylene propylene diene monomer (EPDM) sold under the trade name SANTOPRENE® by Advanced Elastomer Systems may also be used.

A preferred TPE for the sleeve of the invention is a dynamically vulcanized alloy of polyisoprene and polyolefin, most preferably polyisoprene-polypropylene available experimentally from Advanced Elastomer Systems.

Because TPE is thermoplastic, any conventional molding process can be used to make the sleeve of the invention, and the choice of injection, compression or transfer molding may be based on the properties of the particular TPE. Injection molding is generally preferred because the shear stress aids flow of the TPE through leaders and gates into the mold. Selection of molding process and parameters is well within the purview of one skilled in the molding arts and no further details regarding this aspect of the invention are needed.

The sleeve may have a wall thickness of about 0.3 to 1.0, preferably about 0.5 to 0.7 mm. Sleeves within this range, regardless of the molding process and TPE selected, may be made in a molding cycle time from loading to loading of about 12 to 20 seconds. In contrast conventional sleeves of the same thickness made of thermoset polyisoprene require a total cycle time of about 5 minutes for loading, crosslinking and unloading.

EXAMPLE I

Using a conventional hand-held injection mold, the following TPE's were molded into sleeves 0.6 mm thick. The time required for feeding TPE, forming the sleeve and removing the sleeve to ready the mold for a subsequent TPE feeding was about 12–20 sec.

1.) styrene-ethylene-butadiene-styrene (KRATON® G-2712X)

2. ) polypropylene alloy-ethylene-propylene diene monomer (SANTOPRENE® 211-45)

3.) polyisoprene polypropylene alloy.

EXAMPLE II

The sleeves from Example I were mounted onto 22 gauge needles, the needles were epoxied to hubs and the hubs threaded onto needle holders. The distal ends of the needles were submerged in water and an evacuated tube was inserted into each holder and advanced until the proximal end of the needle punctured both the sleeve and the tube closure. Water was drawn into the tube. The tube was removed from the holder. The sleeve was seen to instantly recover to its original position over the needle with no water leakage out of the sleeve, which has resealed itself.

COMPARATIVE EXAMPLE III

When molded in accordance with the process of Example I and tested by the process of Example II, the following TPEs gave sleeves of unsatisfactory elastic recovery and resiliency:

1) all KRATON® and SANTOPRENE® TPEs outside of the specified hardness, tensile and elongation ranges;
2) thermoplastic polyurethane (TPU);
3) thermoplastic polyolefin (TPO).

What is claimed is:

1. A needle holder assembly for collection of a body fluid sample using an evacuated tube comprising:

a) a double-ended needle immobilized in a hub, said needle having proximal and distal ends terminating in points;

b) a tubular needle holder having a first open end for receiving an evacuated tube and a second open end for removably immobilizing said hub; said proximal and extending into said tubular holder when said hub is immobilized thereon; and c) a sleeve over the proximal end of said needle, said sleeve being molded of a resilient and resealable elastomer having a durometer hardness of about 30–60 A, a tensile strength at break of about 300–1,000 psi and an elongation at break of about 200–800% said elastomer being selected from the group consisting of a polyolefin-polyisoprene alloy, styrene-butadiene copolymer, and a vulcanized alloy of polyethylene or polypropylene alloyed with a terpolymer of ethylene-propylene-diene monomer.

2. The assembly of claim 1 wherein said distal end has a point for penetration of a patient's skin.

3. The assembly of claim 1 further comprising a safety shield over said holder.

* * * * *